Aug. 1, 1950 R. CHRISTOFFERSON Plant Pat. 970
PEACH TREE
Filed Nov. 28, 1947
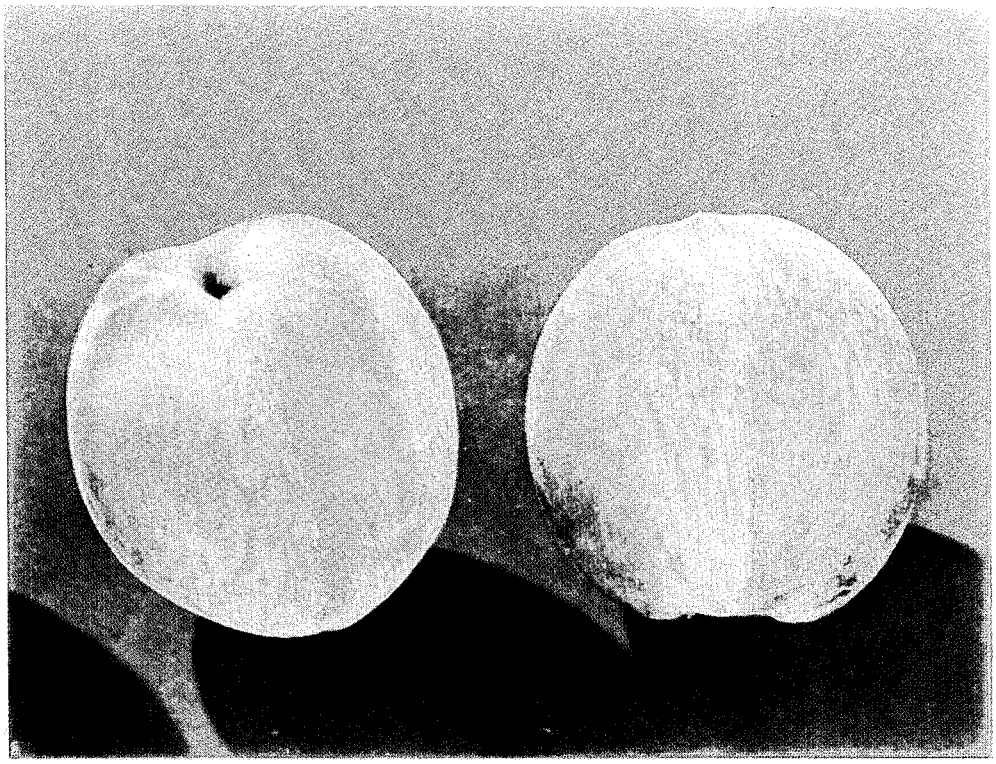
Inventor
R. Christofferson
By Robbins & Robbins
Attorneys Patented Aug. 1, 1950

Plant Pat. 970

UNITED STATES PATENT OFFICE

970

PEACH TREE

Rowland Christofferson, Mountain Home, Ark., assignor to Stark Bro's Nurseries and Orchards Company, Louisiana, Mo., a corporation of Missouri Application November 28, 1947, Serial No. 788,623

1 Claim. (Cl. 47—62)

The present discovery relates to a new and distinct variety of peach tree, originating as a chance seedling.

The outstanding distinctive feature of this new variety resides in the combination of three important characteristics: (1) its early ripening period, (2) its yellow flesh color, and (3) its free stone and good quality character for a peach of its early ripening season.

It may be noted that it is quite unusual to find a yellow flesh color in early ripening peaches and therefore this characteristic in the present peach fills an important commercially desirable demand. Known commercial peaches ripening at approximately the same time as this peach, when grown under comparable conditions, are "Early Red Bird Cling" and "Early Red Free," which ripen about forty-five days before "Elberta," but both of these varieties are white-fleshed and the quality of this new peach is very much better than either or any other known variety of peach ripening at the same time. It is therefore claimed that this new variety is the earliest ripening, high quality, yellow-fleshed, semi-free stone peach known to commerce today. By the term "semi-free stone" I mean in the sense given to it by the trade, that the flesh breaks away from the pit of the ripe fruit, but some strands adhere to the pit as distinguished from the class of semi-clings where the flesh clings tightly to a part of the surface of the pit of ripe fruit, in which case the fruit is clingstone for all practical purposes. With this understanding, this new variety is distinguished from other yellow flesh peach varieties ripening around the same early ripening season, such as "Mikado," "Dixired" and "Marigold" which are not classed as freestones but rather as semi-clings. Furthermore, this variety is distinct from "Mikado" grown under comparable conditions in that the new variety ripens from five to seven days before "Mikado"; and the new variety is distinct from "Marigold" in that the former ripens twelve days ahead of "Marigold" and has a much better flavor than "Marigold," the flesh of which is relatively watery and insipid. This new variety differs from "Dixired" in that the latter is a clingstone and the former a semi-free stone; moreover the present variety has a heavy pubescence while "Dixired" has a very light pubescence.

Asexual reproduction of this new variety shows the foregoing characteristics come true to form and are established.

In the accompanying drawing are shown specimens of this new variety in reverse positions, the yellow color of the skin indicating the yellow flesh color as well known to those skilled in peach culture.

The following is a detailed description of the new variety, color terminology being in accordance with Ridgway's Color Standard, except where otherwise indicated to have ordinary dictionary significance:

*Tree*

Dates first and last picking: July 4th–July 9th, for 1946 season, in Pike County, Illinois.

Medium size; medium vigorous; open; upright; vase formed; hardy; productive; regular bearer.

Trunk: Medium stocky; medium smooth.

Branches: Medium stocky; smooth; three-year old branches Dull Citrine, Plate IV, with Chocolate Brown, color 7'' tone m, Plate XXVIII, mottling.

*Lenticels.*—Medium to few; small.

Leaves: Length, 5''; width, 1½''. Medium large; oval; acutely pointed; medium thick; smooth; Dark Yellowish Green, Plate XVIII.

*Margin.*—Finely serrate.

*Petiole.*—Short; medium slender.

*Glands.*—Average number, 3 to 5. Alternate; small; reniform; free; not pubescent.

Flowers: Medium early compared with other varieties; medium size; pink.

*Fruit*

Maturity when described: Eating; July 10th.

Size: Uniform. Axial diameter, 2¾''. Transverse in suture plane, 2½''. At right angles to suture plane, 2⅜''.

Form: Uniform; oblong; compressed transversely toward suture; side unequal.

*Suture.*—Distinct; shallow; has slight marked depression beyond pistil point.

*Ventral surface.*—Slightly lipped toward apex; lips, equal.

*Cavity.*—Abrupt; suture showing on one side. Depth, ⅜''; breadth, ⅝''. Markings—none.

*Base.*—Rounded.

*Apex.*—Prolonged; apical.

*Stem.*—Length, ⅜''; medium stout; medium strong.

Skin: Medium tough; astringent. Tendency to break—none.

Color: Highly blushed red. Down—abundant; medium length.

Flesh:

*Color.*—Yellow, mottled with red on sunny side throughout. Surface of pit cavity—pink.

*Amygadalin.*—Moderate. Juice—abundant; rich.

*Texture.*—Meaty.

*Fibres.*—Abundant; fine; tender.

*Ripens.*—Fairly even.

*Flavor.*—Subacid.

*Aroma.*—Distinct.

*Eating quality.*—Good.

Stone: Semi-free at maturity.

*Fibres.*—Short; retains short fibre-like threads along ridges.

*Size.*—Medium; length, $1\frac{7}{16}''$; thickness, $\frac{3}{4}''$.

*Form.*—Oval toward base and apex.

*Base.*—Oblique; oval.

*Apex.*—Acuminate.

*Sides.*—Equal; curved on right and left sides.

*Surface.*—Irregularly furrowed near ventral edge toward apex; pitted from base to above center.

*Ridges.*—Rounded toward base and apex.

*Pits.*—Circular to elongated; ventral edge, thick.

*Dorsal edge.*—Narrow; with shallow, narrow groove throughout. Ridges on either side—interrupted.

Use: Market; dessert; canning.

Keeping quality: Medium.

Resistance to:

*Insects.*—Medium.

*Diseases.*—Good.

I claim:

A new and distinct variety of peach tree, characterized as to novelty by the early ripening season and high quality of its fruit, combined with yellow flesh color and free stone characteristics in such early ripening fruit, substantially as shown and described.

ROWLAND CHRISTOFFERSON.

No references cited.